United States Patent
Nuspliger

(10) Patent No.: US 7,142,298 B2
(45) Date of Patent: Nov. 28, 2006

(54) PARTICULATE MONITOR

(75) Inventor: Robert J. Nuspliger, Oak Ridge, TN (US)

(73) Assignee: Shaw Intellectual Property Holdings, Inc., Baton Rouge, LA (US)

( * ) Notice: Subject to any disclaimer, the term of this patent is extended or adjusted under 35 U.S.C. 154(b) by 520 days.

(21) Appl. No.: 10/673,714

(22) Filed: Sep. 29, 2003

(65) Prior Publication Data
US 2005/0068527 A1    Mar. 31, 2005

(51) Int. Cl.
*G01N 21/51* (2006.01)

(52) U.S. Cl. .................................... 356/338
(58) Field of Classification Search ................ None
See application file for complete search history.

(56) References Cited

U.S. PATENT DOCUMENTS

| | | | |
|---|---|---|---|
| 4,017,186 A | 4/1977 | Shofner et al. | |
| 4,140,395 A | 2/1979 | Kreikebaum | |
| 4,176,960 A | 12/1979 | Eckbreth et al. | |
| 4,269,518 A | 5/1981 | Rahn | |
| 4,482,247 A | 11/1984 | Meltz et al. | |
| 4,963,021 A | 10/1990 | Nakamura et al. | |
| 5,056,918 A | 10/1991 | Bott et al. | |
| 5,063,301 A | 11/1991 | Turkevich et al. | |
| 5,085,500 A | 2/1992 | Blesener | |
| 5,104,221 A | 4/1992 | Bott et al. | |
| 5,202,570 A | 4/1993 | Tanaka et al. | |
| 5,298,968 A | 3/1994 | Cheung | |
| 5,371,585 A * | 12/1994 | Morgan et al. | 356/246 |
| 5,373,160 A | 12/1994 | Taylor | |
| 5,731,875 A | 3/1998 | Chandler et al. | |
| 5,777,734 A | 7/1998 | Flower et al. | |
| 5,805,278 A | 9/1998 | Danko | |
| 5,831,730 A | 11/1998 | Traina et al. | |
| 5,999,257 A | 12/1999 | Myers et al. | |
| 6,055,052 A | 4/2000 | Lilienfeld | |
| 6,064,480 A * | 5/2000 | Mountain et al. | 356/335 |
| 6,456,375 B1 | 9/2002 | Ottens et al. | |
| 6,476,911 B1 | 11/2002 | Rose | |
| 6,743,634 B1 * | 6/2004 | Kramer | 436/63 |
| 2001/0035952 A1 | 11/2001 | Merklein | |

* cited by examiner

*Primary Examiner*—Tu T. Nguyen
(74) *Attorney, Agent, or Firm*—Luedeka, Neely & Graham, P.C.

(57) ABSTRACT

A non-extractive optical particulate monitor for measuring particulate matter entrained in a flow within a smokestack, the monitor includes a light emission system which projects a beam of light into the smokestack, a light detection system positioned in a non co-linear relationship with the light emission system to receive and detect light scattered by the particulate matter in the smokestack, and a calibration system located between the light emission system and the light detection system to selectively enable light from the light emission system access to the light detection system without traveling through the flow structure for calibration of the monitor.

25 Claims, 5 Drawing Sheets

PARTICULATE MONITOR

FIELD OF THE INVENTION

This invention relates generally to particulate monitors. More particularly, this invention relates to non-extractive optical devices suitable for measuring particulate matter entrained in a flow, such as in a smokestack environment.

BACKGROUND AND SUMMARY OF THE INVENTION

Measurement of particulate matter, such as particulate matter entrained in a flow of gas, is important for a number of reasons. In the industrial setting, for example, government regulations specify permissible parameters for amounts of particulate matter that may be exhausted to the atmosphere. Non-extractive optical particulate monitors for these purposes are well known, however, improvement is desired.

The present invention relates to an improved non-extractive optical particulate monitor for measuring particulate matter entrained in a flow, such as a flow in a smokestack.

In a preferred embodiment, the monitor includes a light emission system which projects a beam of light into the smokestack. A light detection system is positioned laterally of the beam to receive and detect light scattered by the particulate matter in the smokestack. A calibration system is located between the light emission system and the light detection system. Light from the light emission system accesses the light detection system through the calibration system for calibration of the monitor without traveling through the flow structure.

In yet another aspect, the invention relates to a method for checking operating conditions of an optical monitor configured for monitoring particulate matter in a flow conduit. The steps include providing an optical monitor having a light source and a light detection system. The light detection system includes a collector lens having principal planes. Light is directed from the light source to the light detection system via a path that does not travel through the flow conduit. The light directed to the light detection system is directed in a plane approximately parallel to the principal planes of the collector lens to yield information corresponding to the cleanliness of the collector lens.

A significant advantage of the invention is that it is configured so that it can be mounted externally to a smokestack. Other advantages include minimization of exposed surfaces, simplification of moving parts, and identification of dirty monitor conditions.

BRIEF DESCRIPTION OF THE DRAWINGS

Further features of preferred embodiments of the invention will become apparent by reference to the detailed description of preferred embodiments when considered in conjunction with the figures, which are not to scale, wherein like reference numbers, indicate like elements through the several views, and wherein.

DETAILED DESCRIPTION

Figure 1:
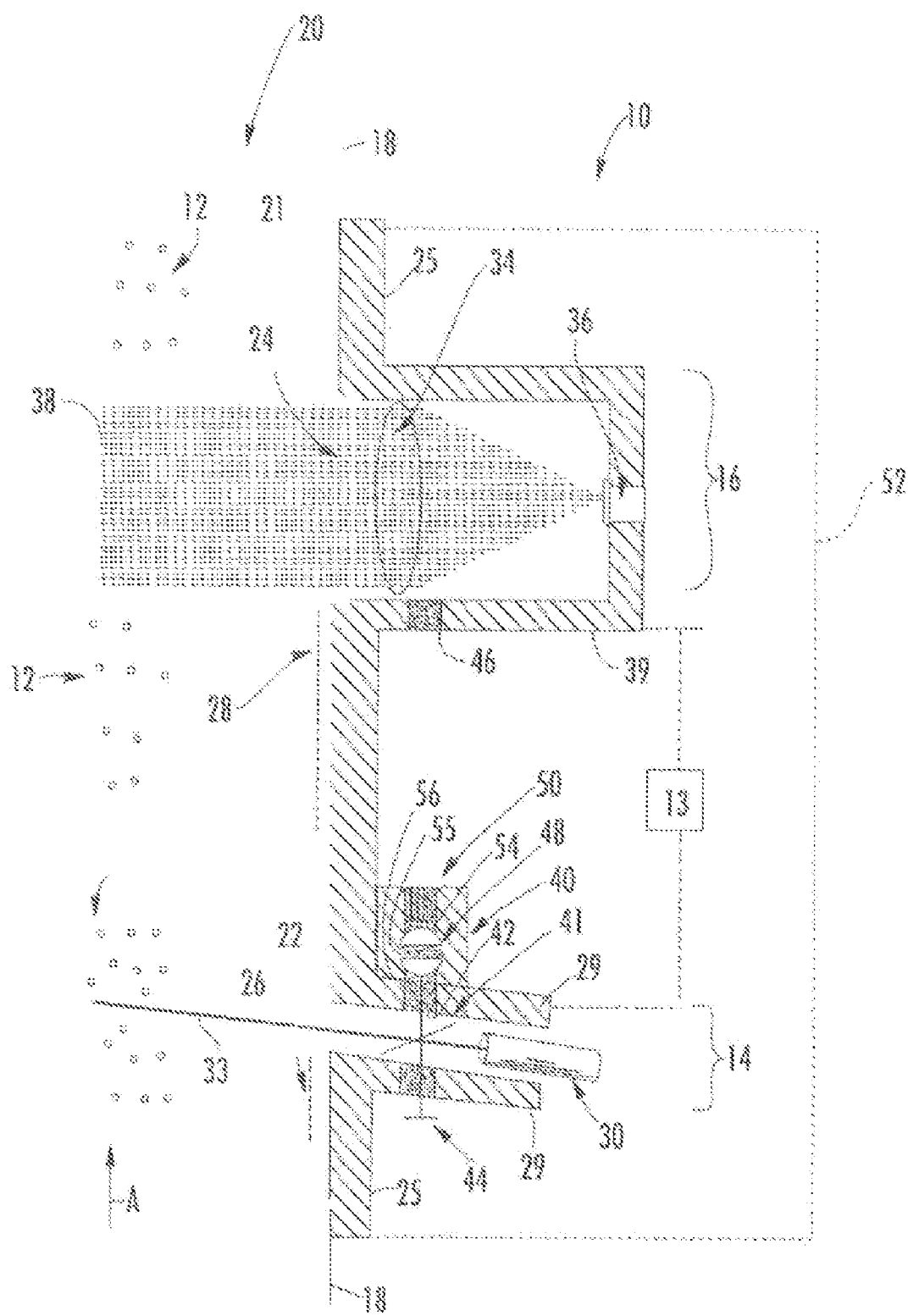
FIG. 1 is a diagrammatic view showing a particulate monitor in accordance with a preferred embodiment of the invention.

With initial reference to FIG. 1, the invention relates to a device 10 for measuring particulate matter, such as particulate matter 12 entrained in a flow within a flow vessel or conduit, such as a smokestack and generally traveling in the direction of arrow A. The device 10 is suitable for a wide variety of uses including, but not limited to, regulatory monitoring of the emissions from fossil fuel combustion sources, monitoring of output emissions of power and recovery boilers in the lumber and paper industries, detection of the presence of undesirable substances in process lines, such as the presence of sulfuric acid mist in chemical processing plants, to aid in troubleshooting pollution control equipment, and for improving plant efficiency by monitoring lost product in manufacturing processes, such as in metals processing plants. The device 10 may be mounted at a single location or used as a portable unit, operated continuously, or periodically as desired.

The device 10 includes a light emitting system 14 and a light detection system 16 laterally spaced (not co-linear) with the light emitting system 14. The device 10 is preferably mounted externally to a sidewall 18 of a flow conduit, such as smokestack 20. The smokestack 20 may be modified for mounting of the device 10 in a manner which enables optical communication between the interior of the smokestack and the light emitting system 14 and the light detecting system 16. For example, the smokestack may have one or more apertures 21 for enabling optical access for the light emitting system 14 and the light detecting system 16 to the interior of the smokestack 20.

Apertures 22 and 24 are provided through a mounting member 25 of the device 10 and aligned with the aperture 21 to enable the systems 14 and 16 to be in optical communication with the smokestack 20. A pair of preferably electronically controlled shutters 26 and 28 cooperate with the apertures 22 and 24, respectively, for selectively sealing the apertures 22, 24, as will be described below.

The light emitting system 14 is located within a housing 29 which preferably surrounds the mounting member 25 to isolate the systems 14 and 16 from the ambient environment. The system 14 includes a light source 30 preferably including a lens device to direct the light in a desired manner. For example, the light source preferably includes a collimator lens adjacent the light source 30 to project a collimated beam of light 33 into the smokestack 20. The beam of light 33 passes through an optically defined sampling volume within the smokestack 20. Particulate matter within the sampling volume causes incident light scattering. Backscattered light is detected by the detection system 16 to yield information corresponding to the mass concentration of particulate matter in the sampling volume. The detection system 16 is preferably positioned laterally to the beam 33, and is oriented to detect light traveling in a path that intersects the beam 33.

The light source 30 is preferably electronically powered and, most preferably, is provided as by a light emitting diode or a laser which emits light in the wavelength region of from about 4,000 to about 1,600 angstroms. The light source 30 may be operated continuously or in pulsed intervals and examples of additional suitable light sources and operational parameters include those described in U.S. Pat. No. 4,017, 186, entitled ELECTRO-OPTICAL METHOD AND SYSTEM FOR IN SITU MEASUREMENTS OF PARTICULATE MASS DENSITY, incorporated herein by reference in its entirety. The collimator lens is selected to be compatible with the light source to provide a well collimated beam of light in the sampling region, with various types of lens systems being suitable including, but not limited to, aspheric lens singlets and multi-component spherical lenses.

The light detection system 16 includes a collector lens 34 and a detector 36. The lens 34 focuses backscattered light 38 onto the detector 36. The detector 36 is preferably a photosensitive device, such as a photodetector, which converts light into electrical signals to yield output signals. The light detection system 16 is preferably located within a detector housing 39.

Output signals from the detector 36 corresponding to the backscattered light 38 may be further processed by suitable processing circuitry, filters, amplifiers, and the like. The output signals from the detector 36 are accordingly processed to yield information corresponding to the mass concentration of the particulate matter and examples of suitable processing techniques are described in U.S. Pat. No. 4,017,186, entitled ELECTRO-OPTICAL METHOD AND SYSTEM FOR IN SITU MEASUREMENTS OF PARTICULATE MASS DENSITY, incorporated herein by reference in its entirety. The collector lens 34 may preferably be a 30 mm dia.×50 mm focal length plano-convex lens. The detector 36 may preferably be a silicon photo diode located coaxially with the collector lens at a distance approximately equal to the focal length.

The device 10 is preferably calibrated at a "zero" point corresponding to blackout or zero light conditions and a "span" point corresponding to the highest light conditions wherein a small portion of the light from the light source 30 is directly transmitted to the light detection system 16 without traveling into the smokestack 20.

To achieve this, the device 10 preferably includes a rotary shutter system 40, a beam splitter 41, an aperture 42 through the housing 29 for permitting light to travel into the shutter system 40 from the light emitting system 14, a mirror 44 for directing light toward the aperture 42, and an elongated slot or aperture 46 through the housing 39 for permitting light passing through the shutter system 40 to enter the light detection system 16. The beam splitter 41 may be a mirror configured for reflecting part of a beam of light and transmitting part of the beam of light.

The shutter system 40 includes a rotary shutter 48 and lens 50, preferably an imaging lens for focusing light in a plane approximately perpendicular to the principal planes of the collector lens 34 while at the same time de-focusing light in a plane approximately parallel to the principal planes of the collector lens 34. In this manner, the lens 50 directs light to travel through the aperture 46 and enter the detector system on the back or detector side of the collector lens 34. The result is a line beam of light that is directed in a plane approximately parallel to the principal planes of the collector lens 34.

An external housing 52 preferably encloses the device 10 so that sunlight and light from sources external to the light system 14 cannot enter the detection system 16. The rotary shutter 48 preferably includes a cylindrical member 54 having an aperture 55 therethrough and rotatably mounted within a cylindrical bore 56. The member 54 is rotated to align the aperture 55 parallel with the bore 56 for unrestricted passage of light and perpendicular to the bore 56 for substantially complete restriction of light passage therethrough. Varying degrees of light restriction may be achieved by varying the rotation of the member 55.

To achieve a zero point calibration, the shutters 26 and 28 and the rotary shutter 48 are closed so that substantially no light enters the detection system. Then, the detector 36 produces a signal corresponding to zero light, which provides a zero reference and corresponds to substantially all sources of noise.

Figure 2A:
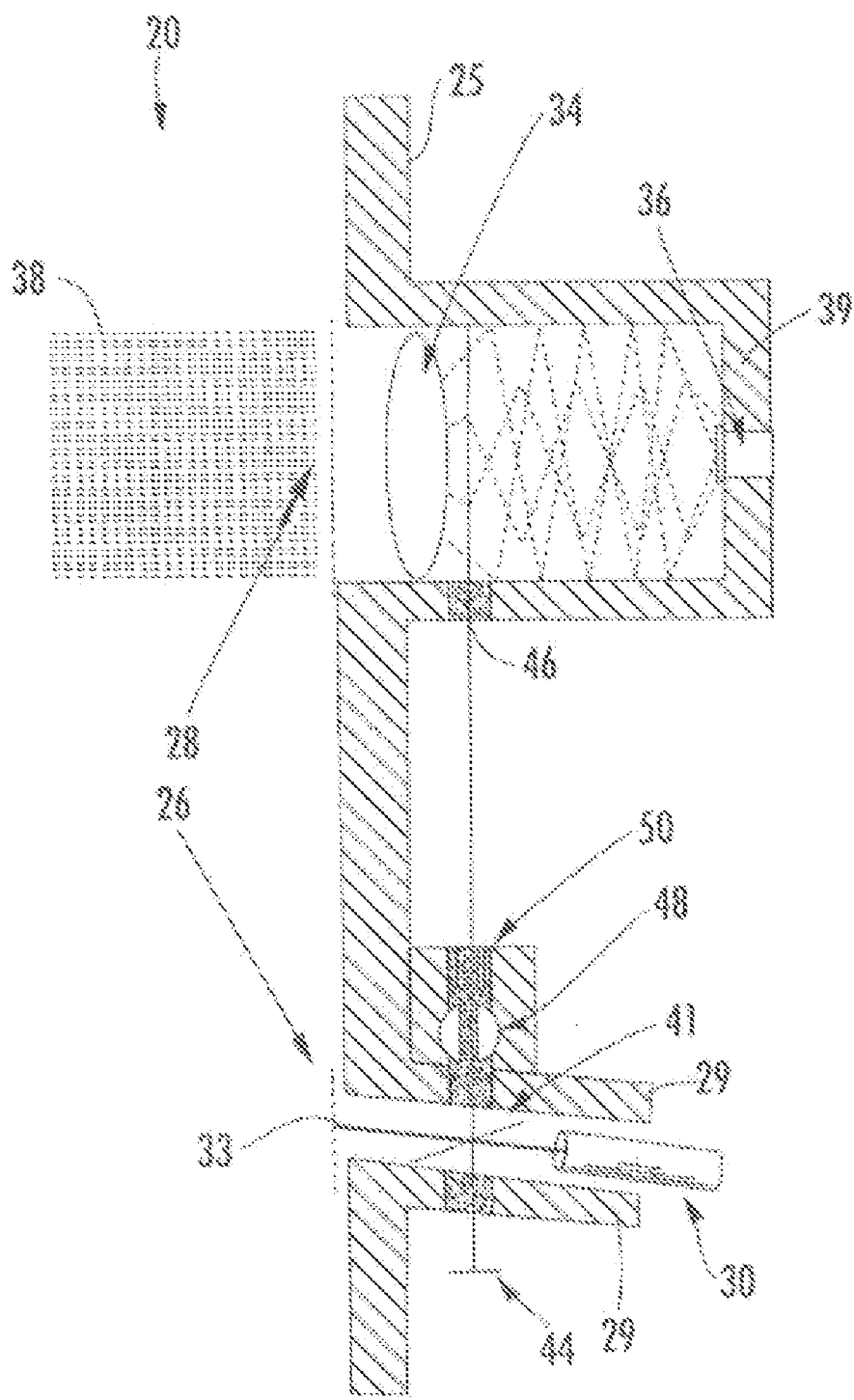
FIG. 2A is a diagrammatic view of the particulate monitor of FIG. 1 in a calibration mode.

With reference to FIG. 2A, and in connection with performance of a span point calibration, the rotary shutter 48 is opened and light is transmitted by the light source 30 and reflected off the beam splitter 41 to the mirror 44. Light striking the mirror 44 is reflected back to the beam splitter 41, and part of the light is transmitted through the beam splitter 41. The lens 50 preferably focuses light in a plane approximately perpendicular to the principal planes of the collector lens 34 while at the same time de-focuses light in a plane approximately parallel to the principal planes of the collector lens 34. This yields a line beam of light that is directed in a plane approximately parallel to the principal planes of the collector lens 34, with a portion of such light reaching the detector 36 to provide a signal corresponding to these span conditions. As shown in FIG. 2A, light entering through aperture 46 is reflected by the interior of housing 39 and the lens 34 until a portion of the light strikes the detector 36.

Figure 2B:
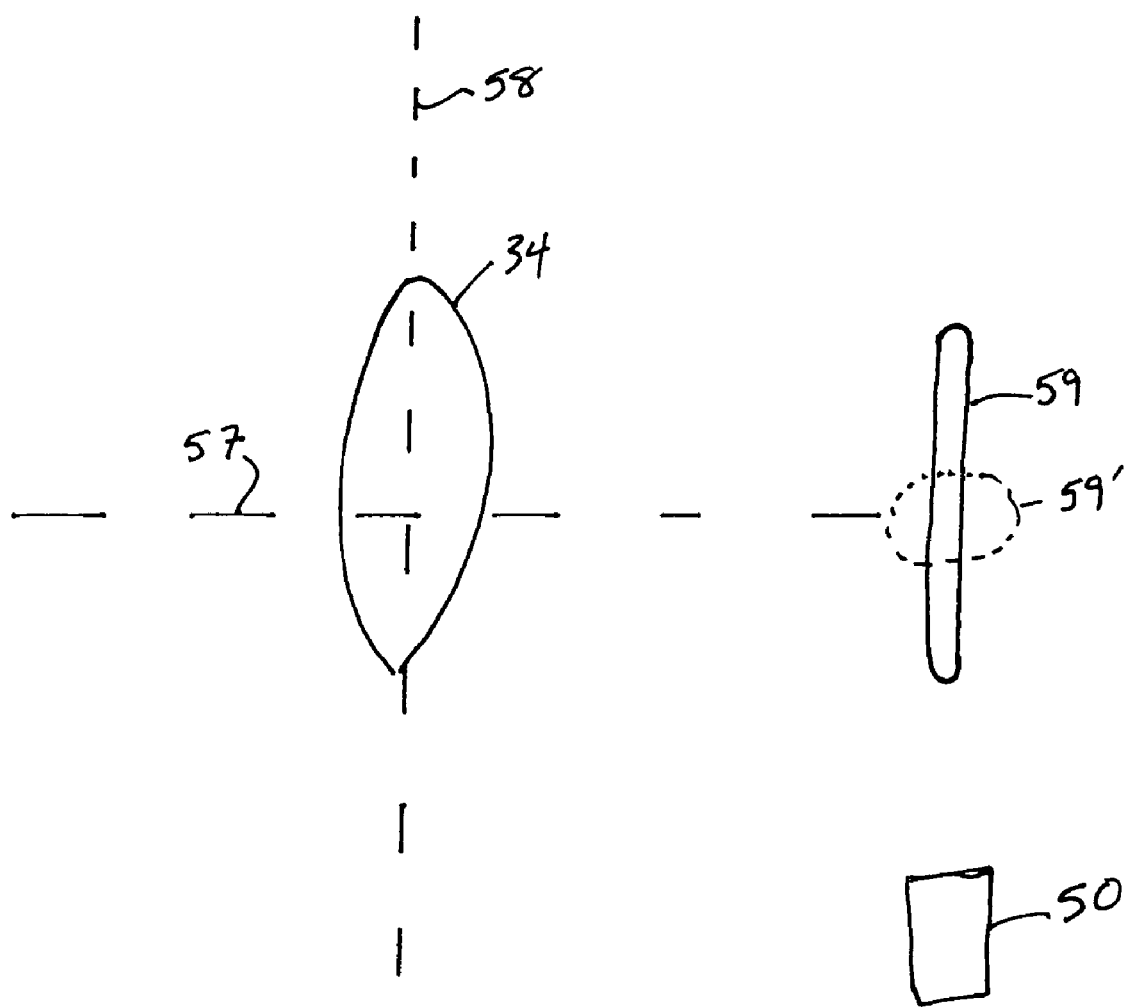
FIG. 2B is a representational view illustrating the principal planes of the collector lens and focusing of the light beam relative thereto.

FIG. 2B is provided to illustrate the principal planes of the collector lens and the function of the lens 50 to direct the light in a plane approximately parallel to the principal planes of the collector lens. In this regard, it is noted that there are generally two planes perpendicular to the optical axis of a lens, and which are typically referred to as the "primary principal plane" and the "secondary principal plane." These "principal planes" are shifted generally to the front and rear of the lens, but are parallel to one another.

With reference to FIG. 2B, there is shown a plane indicated by dashed line 57 which will be understood to be generally perpendicular to the principal planes of the collector lens 34. The plane indicated by dashed line 58 is generally parallel to the principal planes of the collector lens 34. A beam of light 59 emitted from the lens 50 is shown to be a collimated or line beam. The beam of light 59 is focused in a plane approximately perpendicular to the principal planes of the collector lens. Reference numeral 59' depicts a beam of light that is not collimated. As will be noted, the beam 59' is not collimated and is generally round. Thus, it will be appreciated that the lens 50 serves to focus light in a plane approximately perpendicular to the principal planes of the collector lens 34 while at the same time the lens de-focuses or spreads light in a plane approximately parallel to the principal planes of the collector lens 34, to yield the line beam 59 that is directed in a plane approximately parallel to the principal planes of the collector lens 34.

The span point calibration also advantageously provides information concerning the condition of optical surfaces exposed to the smokestack during normal operation, e.g., the side of the beam splitter 41 and the side of the lens 34 which face the smokestack flow. For example, a change in light intensity, i.e., a change in signal amplitude measured by the detector 36, between subsequent span calibrations can indicate that one or more of the optical surfaces has become dirty and needs to be cleaned. For example, if the lens 34 has become dirty it will scatter a different amount of the light entering aperture 46 thereby changing the amount of light that will strike the detector 36.

With further reference to FIG. 1, the device 10 preferably includes a control system 13 including suitable electronics, computer controllers, actuators, motors, and the like for controlling operation of the device, such powering the light source, controlling the operation of the shutters and rotary shutter, operation of the detector and processing of detector signals, and the like.

Figure 3:
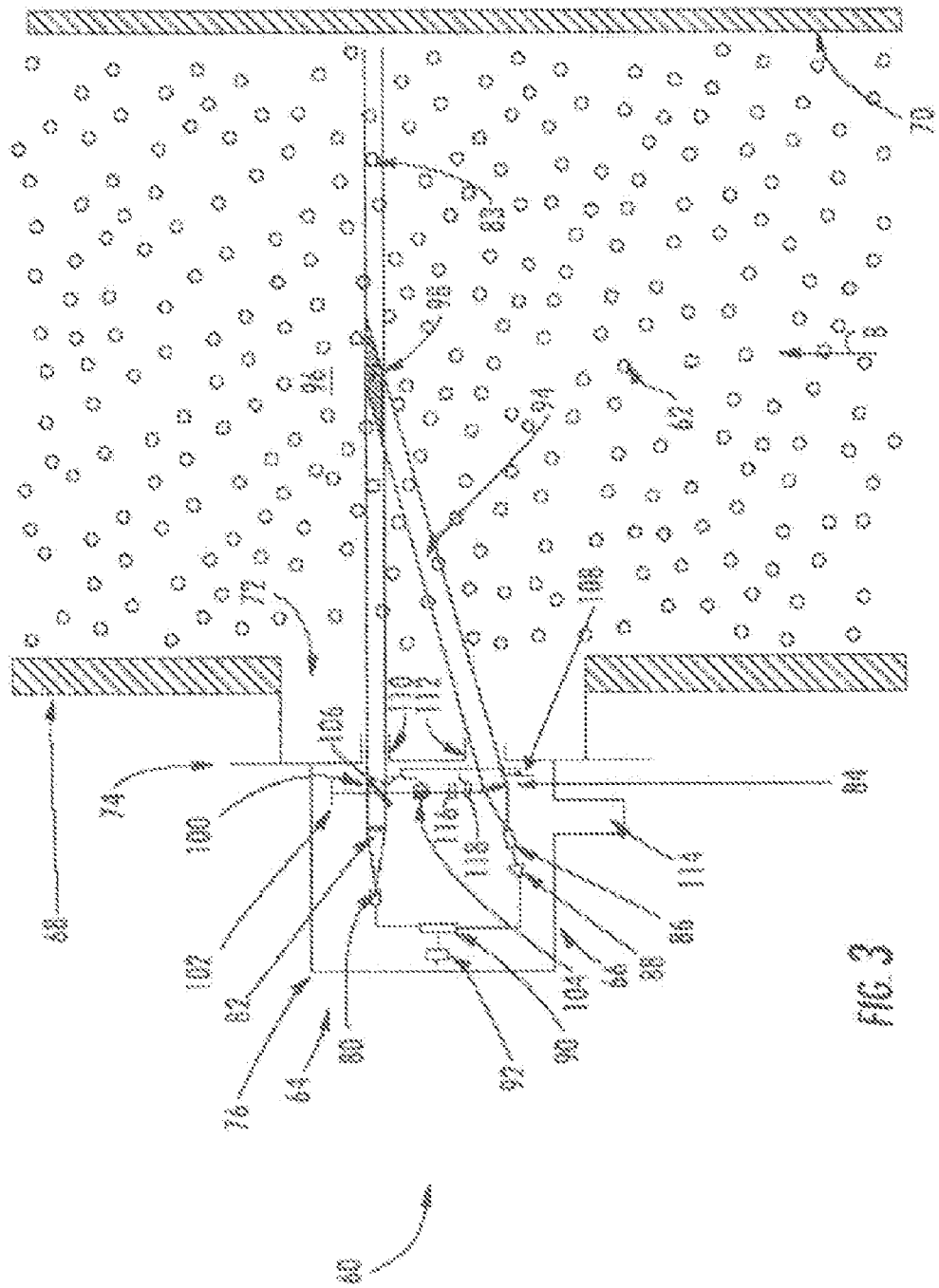
FIG. 3 shows a particulate monitor in accordance with an alternate embodiment of the invention.

With reference now to FIG. 3, there is shown an alternate embodiment of a device 60 for measuring particulate matter 62 entrained in a flow traveling generally in the direction of arrow B.

The device 60 includes a light emitting system 64 and a light detection system 66 laterally spaced (not co-linear) with the light emitting system 64. The device 60 is preferably mounted entirely external to a sidewall 68 of a flow conduit, such as smokestack 70. In this regard, aperture 72 extends through the sidewall 68 of the smokestack 70. A mounting flange 74 is disposed on the aperture 72 for mounting of the device 60 and a housing 76 encloses the components of the device 60.

The light emitting system 64 includes a light source 80 and a lens device, such as a collimator lens 82, cooperating with the light source 80 to project a collimated beam of light 83 into the smokestack 70. The light source 80 preferably substantially corresponds to the light source 30 described previously.

The light detection system 66 includes a collector lens 84 and a detector 86, which preferably substantially corresponds to the collector lens 34 and detector 36 described previously. The light detection system 66 also preferably includes an amplifier 88 controlled by processing electronics 90 to provide output signals to an electrical signal output 92.

The orientation and configuration of the lens 84 and detector 86 define a return light optical beam path 94. The path 94 is directed at a portion of the collimated light beam 83 within a sampling volume area 96 of the smokestack 70. Light scattered from particulate matter 62 within intersection 98 of the optical paths 83 and 94 is returned via the optical path 94 through the collector lens 84 and to the detector 86. The electrical signal from the detector 86 passes through the amplifier 88 under control of the processing electronics 90. The light source 80 and/or the return signal from the amplifier 88 may be modulated/demodulated by the processing electronics to reduce or eliminate effects from other inadvertent sources of light on the output of the electrical signal output 92.

The device 60 also preferably includes, for calibration purposes, an optical beam splitter 100, a mirror 102, and a rotary shutter system 104. The optical beam splitter 100, mirror 102, and shutter system 104 are preferably similar to the beam splitter 41, mirror 44, and the rotary shutter system 40 described previously. The beam splitter 100 is inserted into the collimated beam of light 83, which causes a portion of light to be reflected to the mirror 102, which is preferably located parallel to and spaced away from the beam of light 83, adjacent the beam splitter 100. Reflected light from the mirror 102 passes back through the beam splitter 100 to the rotary shutter system 104, which is closed during normal operation and opened, as described below, for certain calibration purposes.

Shutters 106 and 108 are associated with ports 110 and 112 of the mounting flange 74. The shutters 106 and 108 are used during calibration and or protecting the light emitting and detection systems in certain events. For example, it is preferred that the system 60 include a purge air system having an air inlet 114 and associated blower unit for introducing purge air. The purge air may be exhausted through the ports 110 and 112. The purge air is useful for temperature control of the device 10, e.g., protecting it from the heat of the smokestack gasses, and to inhibit dust and particulate accumulation on exposed optical surfaces of the device 60, such as the beam splitter 100 and the collector lens 84. In the event of a loss of the purge air, or when the device 10 is shut down, it is preferred that the shutters 106 and 108 be closed to protect the device 60.

For the reasons described previously, it is preferred to have zero and span calibration points. To obtain a zero calibration point, the shutters 106 and 108 are closed and the rotary shutter system 104 closed to prevent light from the light source 80 from reaching the detector 86. If desired, the zero point may be adjusted by the processing electronics 90.

An upscale or span calibration point may be obtained by inserting the beam splitter 100 into the beam of light 83 and opening the rotary shutter system 104. Light is reflected off the beam splitter 100 to the mirror 102, back through the beam splitter 100 and through the rotary shutter system 104. The shutter system 104 may be opened varying amounts to allow all or varying parts to the reflected light to pass. In this regard, additional optical devices, such as a lens 116 is preferably located adjacent shutter system 104 to yield a line beam of light that is directed in a plane approximately parallel to the principal planes of the collector lens 84.

A beam steering device 118 is preferably included adjacent the lens 116 to precisely position the beam of light onto the back surface of the collector lens 84 such that most, if not substantially all of the front of the collector lens 84 is illuminated. Light reflected from the front and rear surfaces of the lens 84 is scattered in many directions, with a small portion of this scattered light reaching the detector 86 to provide a span point signal. The amplitude of this signal may be adjusted by changing the position of the mirror 102 and/or the beam splitter 100 and/or the shutter system 104.

It will be appreciated that the rotary shutter system 104 further enables multiple span calibration points. For example, the rotary shutter system 104 may be oriented in various positions relative to the light beam passing through it. In this regard, and with reference to FIG. 4, the shutter system 104 may include a plurality of mechanical stops 120 to enable a plurality of fixed shutter positions relative to the beam of light.

In addition to providing one or more span calibration points, the above described span calibration steps also enables a check of the condition of the optical surfaces exposed to smokestack gasses during normal operation, such as surfaces of the beam splitter 100 and the collector lens 84.

During the calibration step, light is reflected from the beam splitter 100 to the mirror 102 and back through the beam splitter 100 in the same area as the beam of light 83 passes through the beam splitter 100. Thus, any changes in the condition of the surfaces of the beam splitter 100 which affects the intensity of the beam of light 83 will also affect the light beam measured by the detector 86 during the span calibration step.

Also, and for example, dust particles on the front surface of the collector lens 84 (the surface facing the smokestack) will tend to scatter light in many directions. Some of this scattered light will reach the detector 86, thus resulting in a change, generally an increase, in the amplitude signal as compared to the signal that would be obtained absent the dust particles.

Figure 4:
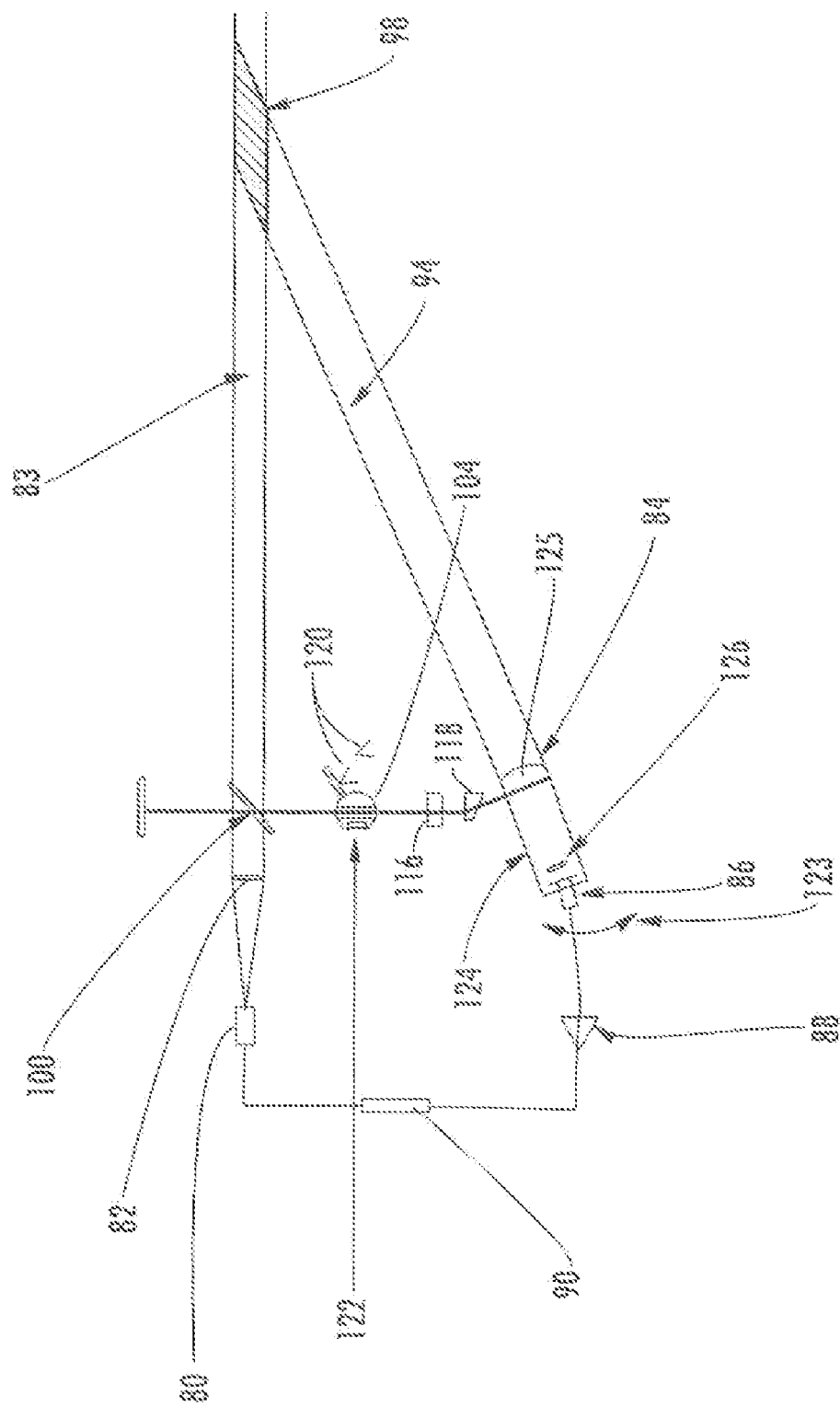
FIG. 4 shows the particulate monitor of FIG. 3 incorporating additional improvement features in accordance with further embodiments of the invention.

With additional reference to FIG. 4, the monitor may also preferably include a detector, such as photo sensitive detector 122 embedded in the rotary shutter system 104 so that during normal operation, with the rotary shutter system 104 oriented to fully restrict the passage of light therethrough, the detector 122 receives an optical signal which is proportional to the beam of light 83 from the light source 80. This optical signal may be used, for example, in conjunction with the processing electronics 90 to monitor and/or control the output of the light source 80, or to indicate system faults.

In addition, the monitor may be configured to enable variation of the sampling region as by motion indicated generally by reference numeral 123. For example, and with continued reference to FIG. 4, a housing 124 associated with the light detection system and enclosing the lens 84 and detector 86 may be pivotally mounted about a point, such as point 125, so that its position may be adjusted to change the location of the intersection 98, along the length of the beam of light 83.

In yet another aspect, a filter, such as an optical bandwidth filter 126, is located in front of the detector 86. The bandwidth of the filter 126 is preferably sufficient to allow light at the wavelength(s) of the light emitted by the light source 80 to pass through the detector 86, while rejecting most, if not all, light from other sources having different wavelengths.

As will be appreciated, monitors in accordance with the invention have numerous advantages over previous monitors. For example, the monitors are mounted external to the smokestack environment and operation of the monitor, including calibration, is accomplished without movement of any of the primary optical components of the system, such as the light source, collector lens, and detector. The invention also advantageously enables identification of monitor conditions requiring maintenance, such as cleaning of lens surfaces.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A non-extractive optical particulate monitor for measuring particulate matter entrained in a flow within a flow structure, the monitor comprising:
   a light emission system located adjacent to and placeable in optical communication with the flow structure and including a light source positioned to project a beam of light into the flow structure, wherein the beam of light is scattered by particulate matter;
   a light detection system having a detector and located adjacent to and placeable in optical communication with the flow structure and positioned in a lateral relationship with the light emission system for receiving a desired portion of the light scattered by the particulate matter; and
   a calibration system including a calibration shutter located between the light emission system and the light detection system and remote from the flow structure to selectively admit light from the light emission system to enter the light detection system for calibration of the monitor without traveling through the flow structure.

2. The monitor of claim 1, further comprising one or more shutters adjacent the flow structure and operable to selectively block optical communication between the light emission system and the flow structure and optical communication between the light detection system and the flow structure so as to provide a barrier to the travel of light from the light emission system into the flow structure and a barrier to the travel of light from the flow structure to the light detection system.

3. The monitor of claim 1, wherein the light emission system further comprises a lens associated with the light source for acting on light received from the light source to yield a collimated beam of light.

4. The monitor of claim 1, wherein the light detection system further comprises a collector lens for directing scattered light toward the detector.

5. The monitor of claim 1, wherein the calibration shutter comprises a rotary shutter and the calibration system further comprises a beam splitter and a mirror operatively associated with the light source of the light emission system and positioned adjacent a first end of the calibration shutter for directing light toward the calibration shutter.

6. The monitor of claim 5, wherein the light detection system further includes a collector lens having principal planes and the calibration system further includes a lens for directing light emitted from the calibration shutter in a plane approximately parallel to the principal planes of the collector lens.

7. The monitor of claim 1, further comprising a first aperture adjacent the light emission system for providing an optical communication path between the light emission system and the flow structure and a second aperture adjacent the light detection system for providing an optical communication path between the light detection system and the flow structure.

8. The monitor of claim 7, further comprising a first shutter adjacent the first aperture and operable to selectively close the first aperture and provide a barrier to the travel of light from the light emission system into the flow structure and a second shutter adjacent the second aperture and operable to selectively close the second aperture and provide a barrier to the travel of light from the flow structure to the light detection system.

9. The monitor of claim 1, wherein the calibration system is operable to provide a zero point calibration under conditions wherein substantially no light from the light emission system enters the light detection system, and a span point calibration wherein light from the light emission system is directed to the light detection system without traveling through the flow structure.

10. A non-extractive optical particulate monitor for measuring particulate matter entrained in a flow within a flow conduit, the monitor comprising a light emission system which projects a beam of light into the flow conduit, wherein such light is scattered by the particulate matter, a light detection system positioned in a non co-linear relationship with the light emission system to receive and detect light scattered by the particulate matter in the flow conduit, and a calibration system located between the light emission system and the light detection system to selectively enable light from the light emission system access to the light detection system without traveling through the flow structure for calibration of the monitor.

11. The monitor of claim 10, wherein the light emission system comprises a light source and a collimator lens adjacent the light source for projecting a collimated beam of light into the flow conduit.

12. The monitor of claim 10, wherein the light emission system is mounted external to the flow conduit and the flow conduit includes a light emission aperture for permitting light from the light detection system to enter the flow conduit.

13. The monitor of claim 12, further comprising a shutter adjacent the light emission aperture to block the travel of light from the light emission system into the flow conduit.

14. The monitor of claim 10, wherein the light detection system comprises a collector lens and a detector adjacent the collector lens.

15. The monitor of claim 10, wherein the light detection system is mounted external to the flow conduit and the flow conduit includes a light detection aperture for permitting light from the flow conduit to enter the light detection system.

16. The monitor of claim 15, further comprising a shutter adjacent the light detection aperture to block the travel of light from the flow conduit into the light emission system.

17. The monitor of claim 10, wherein the calibration system includes a beam splitter and a mirror operatively associated with the light emission system for generating a calibration light beam, and a rotary shutter system located between the light emission system and the light detection system for selectively transmitting the calibration light beam or a desired portion thereof to the light detection system.

18. The monitor of claim 17, wherein the light detection system further includes a collector lens having principal planes and the rotary shutter system comprises a rotary shutter and a lens adjacent the rotary shutter for directing light emitted from the rotary shutter in a plane generally parallel to the principal planes of the collector lens.

19. The monitor of claim 10, wherein the calibration system is operable to provide a zero point calibration under conditions wherein substantially no light from the light emission system enters the light detection system, and a span point calibration wherein light from the light emission system is directed to the light detection system without traveling through the flow structure.

20. A system for measuring particulate matter, the system comprising:
  a flow structure for receiving a flow therein containing particulate matter;
  a first aperture for emitting light into the flow structure and a second aperture for enabling light to travel from the flow structure;
  a light emission system located external to the flow structure and including a light source and an associated collimator lens positioned to project a beam of light into the flow structure through the first aperture, wherein the beam of light is scattered by the particulate matter;
  a light detection system located adjacent the second aperture and external to the flow structure in a lateral relationship with the light emission system, the light detection system including a detector and a collector lens having principal planes; and
  a calibration system comprising a beam splitter, a mirror operatively associated with the light emission system for generating a calibration light beam, and a rotary shutter system located between the light emission system and the light detection system for selectively transmitting the calibration light beam or a desired portion thereof to the light detection system, the rotary shutter system including a rotary shutter for directing light in a plane generally parallel to the principal planes of the collector lens.

21. The monitor of claim 20, further comprising a photosensitive detector operatively associated with the rotary shutter for receiving an optical signal proportional to the beam of light from the light source when the rotary shutter is oriented to fully restrict the passage of light therethrough.

22. The monitor of claim 20, wherein the light detection system is pivotally movable about a point so that its position may be adjusted.

23. The monitor of claim 20, wherein the detector includes an optical bandwidth filter.

24. The monitor of claim 20, further comprising a purge air system having an inlet for introducing air into the monitor and an outlet for exhausting air from the monitor to the flow conduit.

25. A method for checking operating conditions of an optical monitor configured for monitoring particulate matter in a flow conduit, comprising the steps of providing an optical monitor having a light source and a light detection system, with the light detection system including a collector lens having principal planes; directing light from the light source to the light detection system via a path that does not travel through the flow conduit and which is directed in a plane generally parallel to the principal planes of the collector lens to yield information corresponding to the cleanliness of the collector lens.

* * * * *